(12) United States Patent
Guinan

(10) Patent No.: US 7,384,393 B2
(45) Date of Patent: Jun. 10, 2008

(54) VAGINAL SPECULUM

(76) Inventor: William P. Guinan, 501 Porter St., Manchester, CT (US) 06040

( * ) Notice: Subject to any disclaimer, the term of this patent is extended or adjusted under 35 U.S.C. 154(b) by 0 days.

(21) Appl. No.: 11/098,240

(22) Filed: Apr. 4, 2005

(65) Prior Publication Data
US 2006/0224043 A1   Oct. 5, 2006

(51) Int. Cl.
*A61B 1/32* (2006.01)
(52) U.S. Cl. ...................... 600/220; 600/235
(58) Field of Classification Search ............... 600/201, 600/210, 211, 213, 214, 215, 219, 220, 222, 600/225, 226, 235
See application file for complete search history.

(56) References Cited

U.S. PATENT DOCUMENTS

| | | | | |
|---|---|---|---|---|
| 1,066,889 A | * | 7/1913 | Drosin | 600/222 |
| 2,320,709 A | * | 6/1943 | Arnesen | 600/221 |
| 2,374,863 A | | 5/1945 | Guttmann | |
| 2,483,233 A | * | 9/1949 | Price et al. | 600/205 |
| 2,544,932 A | * | 3/1951 | Marco | 600/213 |
| 2,575,253 A | * | 11/1951 | Bicek | 600/210 |
| 2,829,649 A | * | 4/1958 | Glenner | 606/201 |
| 2,954,025 A | * | 9/1960 | Grieshaber | 600/220 |
| 3,110,305 A | * | 11/1963 | Sygnator | 600/222 |
| 3,246,646 A | * | 4/1966 | Murphy, Jr. | 600/222 |
| 3,332,414 A | * | 7/1967 | Gasper | 600/222 |
| 3,528,409 A | * | 9/1970 | Bruder | 600/220 |
| 3,565,061 A | * | 2/1971 | Reynolds et al. | 600/220 |
| 3,575,163 A | * | 4/1971 | Gasper | 600/222 |
| 3,650,266 A | * | 3/1972 | Pestka et al. | 600/222 |
| 3,744,481 A | | 7/1973 | McDonald | |
| 3,752,149 A | * | 8/1973 | Ungar et al. | 600/222 |
| 3,768,460 A | * | 10/1973 | Panzer | 600/220 |
| 3,796,214 A | * | 3/1974 | Davis | 600/205 |
| 3,815,585 A | * | 6/1974 | Fiore | 600/222 |
| 3,817,242 A | * | 6/1974 | Uddenberg | 600/222 |
| 3,851,642 A | | 12/1974 | McDonald | |
| 3,890,961 A | * | 6/1975 | Moore et al. | 600/222 |
| 3,985,125 A | * | 10/1976 | Rose | 600/220 |
| 4,202,324 A | | 5/1980 | Alison | |
| 4,206,750 A | * | 6/1980 | Kaivola | 600/220 |
| 4,226,228 A | * | 10/1980 | Shin et al. | 600/206 |
| 4,263,898 A | * | 4/1981 | Wannag | 600/220 |
| 4,385,626 A | * | 5/1983 | Danz | 600/220 |
| 4,432,351 A | * | 2/1984 | Hoary | 600/220 |
| D274,356 S | * | 6/1984 | Riedell | D24/135 |
| 4,492,220 A | * | 1/1985 | Hayes | 600/203 |
| 4,597,382 A | * | 7/1986 | Perez, Jr. | 600/203 |

(Continued)

*Primary Examiner*—Cary E. O'Connor
*Assistant Examiner*—Jonathan Werner
(74) *Attorney, Agent, or Firm*—Alix, Yale & Ristas, LLP

(57) ABSTRACT

A vaginal speculum having a universal connection between the handle and each of a plurality of blades, for selectively detaching and attaching one or more of the blades at any one of a plurality of angles between the handle axis and the blade axis. Preferably, the vaginal speculum is part of a kit having a plurality of elongated blades adapted to penetrate and fully enter a vagina while providing surgical access, each being interchangeably connectable to the handle, thereby providing a variety of options for blade length, blade width, or blade contour to better fit the vaginal structure of a particular patient. Each blade is made of a rigid or semi-rigid plastic, that is disposable after each use. The handle is preferably made of heavy metal, with a permanent plastic sheath or coating.

8 Claims, 10 Drawing Sheets

U.S. PATENT DOCUMENTS

| | | | |
|---|---|---|---|
| 4,615,334 A * | 10/1986 | Jaeger | 600/195 |
| 4,766,887 A * | 8/1988 | Cecil et al. | 600/222 |
| 4,807,600 A * | 2/1989 | Hayes | 600/203 |
| 4,884,559 A * | 12/1989 | Collins | 600/205 |
| 4,899,734 A * | 2/1990 | Gelley | 600/220 |
| 4,971,036 A * | 11/1990 | Collins | 600/202 |
| 5,007,409 A * | 4/1991 | Pope | 600/203 |
| 5,052,372 A * | 10/1991 | Shapiro | 600/222 |
| 5,063,908 A * | 11/1991 | Collins | 600/187 |
| 5,072,720 A * | 12/1991 | Francis et al. | 600/186 |
| 5,179,938 A * | 1/1993 | Lonky | 600/223 |
| 5,183,032 A | 2/1993 | Villalta et al. | |
| 5,231,973 A * | 8/1993 | Dickie | 600/222 |
| 5,318,010 A * | 6/1994 | Lundberg | 600/222 |
| 5,458,595 A * | 10/1995 | Tadir et al. | 606/15 |
| 5,465,709 A | 11/1995 | Dickie et al. | |
| 5,499,964 A * | 3/1996 | Beck et al. | 600/220 |
| 5,509,893 A * | 4/1996 | Pracas | 600/224 |
| 5,681,325 A | 10/1997 | Hasson | |
| 5,785,648 A | 7/1998 | Min | |
| 5,846,249 A * | 12/1998 | Thompson | 606/119 |
| 5,865,729 A | 2/1999 | Meehan et al. | |
| 5,868,668 A | 2/1999 | Weiss | |
| 5,873,820 A * | 2/1999 | Norell | 600/220 |
| 5,997,474 A * | 12/1999 | Batchelor | 600/220 |
| 6,004,265 A * | 12/1999 | Hsu et al. | 600/223 |
| 6,024,696 A * | 2/2000 | Hoftman et al. | 600/224 |
| 6,024,697 A | 2/2000 | Pisarik | |
| 6,048,308 A * | 4/2000 | Strong | 600/205 |
| 6,120,438 A * | 9/2000 | Rizvi | 600/228 |
| 6,280,379 B1 * | 8/2001 | Resnick | 600/220 |
| 6,354,995 B1 | 3/2002 | Hoftman et al. | |
| 6,364,832 B1 * | 4/2002 | Propp | 600/220 |
| 6,379,299 B1 * | 4/2002 | Borodulin et al. | 600/220 |
| 6,394,950 B1 * | 5/2002 | Weiss | 600/205 |
| 6,416,466 B1 * | 7/2002 | Hsiao | 600/220 |
| 6,428,474 B1 * | 8/2002 | Weiss | 600/224 |
| 6,432,048 B1 * | 8/2002 | Francois | 600/220 |
| 6,450,952 B1 * | 9/2002 | Rioux et al. | 600/223 |
| 6,506,190 B1 | 1/2003 | Walshe | |
| 6,569,091 B2 * | 5/2003 | Diokno et al. | 600/220 |
| 6,589,168 B2 * | 7/2003 | Thompson | 600/221 |
| 6,595,917 B2 * | 7/2003 | Nieto | 600/223 |
| 6,669,654 B2 | 12/2003 | Diokno et al. | |
| 6,702,740 B2 * | 3/2004 | Herold | 600/220 |
| 6,712,761 B2 * | 3/2004 | Borodulin et al. | 600/184 |
| 6,719,687 B1 | 4/2004 | Van Der Weegen | |
| 2002/0022771 A1 * | 2/2002 | Diokno et al. | 600/220 |
| 2002/0055670 A1 * | 5/2002 | Weiss | 600/220 |
| 2002/0115910 A1 * | 8/2002 | Diokno et al. | 600/220 |
| 2002/0169363 A1 * | 11/2002 | Herold | 600/220 |
| 2002/0177791 A1 * | 11/2002 | Diokno et al. | 600/591 |
| 2003/0069477 A1 * | 4/2003 | Raisman et al. | 600/220 |
| 2003/0105387 A1 * | 6/2003 | Frumovitz et al. | 600/220 |
| 2003/0176772 A1 * | 9/2003 | Yang | 600/220 |
| 2004/0054260 A1 * | 3/2004 | Klaassen et al. | 600/220 |
| 2005/0113644 A1 * | 5/2005 | Obenchain et al. | 600/222 |

* cited by examiner

VAGINAL SPECULUM

BACKGROUND OF THE INVENTION

The present invention relates to a weighted vaginal speculum of the type comprising an elongated blade having a contour adapted to penetrate and fully enter a vagina while providing surgical access, and an elongated, weighted handle connected to the blade, for initially manipulating the blade and providing a counter weight to the blade during surgery.

A variety of vaginal specula have been used or described in printed publications, for maintaining access to a female vagina while the surgeon inserts various instruments along or through the blade to perform the necessary procedures within the vagina. Such specula have been adapted for use in conjunction with particular instruments, such as fiber optic cables, and other unique forms of diagnostic, monitoring and incision related equipment. In general these specula have been designed for compatibility with the type of diagnostic or surgical procedure, and in particular for unique instruments and equipment, rather than for the particular characteristics of the patient's anatomy.

From patient to patient, the vagina can vary as to length, width, taper angle, and angle of the vaginal centerline relative to the surface of a surgery table on which the patient lies. In typical vaginal diagnostic or surgical procedures, the doctor or surgeon must adapt the positioning and support of the speculum to the particular characteristics of the patient's vagina. This adaptation is either very time consuming, for example, by selecting one of a plurality of available specula and trying one after the other until a good fit is obtained, or else using a standardized speculum that must be supported in an awkward or less than ideal orientation. Moreover, if multiple specula are tried before the "best fit" is identified, this requires that for each operation multiple specula be available, and multiple specula will require autoclave treatment before reuse.

SUMMARY OF THE INVENTION

It is an object of the present invention to provide a vaginal speculum that is adjustable in the surgical field, as to one or both of blade length and blade angle.

In one embodiment, each of a variety of blades is connectable to a universal handle.

In another embodiment, any particular blade can be secured to a universal handle, at any of a range of angles.

It is a preferred object of the present invention to provide a vaginal speculum having a universal connection between the handle and each of a plurality of blades, for selectively detaching and attaching one or more of the blades at any one of a plurality of angles between the handle axis and the blade axis.

Preferably, the vaginal speculum is part of a kit having a plurality of elongated blades adapted to penetrate and fully enter a vagina while providing surgical access, each being interchangeably connectable to the handle, thereby providing a variety of options for blade length, blade width, or blade contour to better fit the vaginal structure of a particular patient.

In another aspect, each blade is made of a rigid or semi-rigid plastic, that is disposable after each use. The handle is preferably made of heavy metal, with a permanent plastic sheath or coating. Having all the exposed surfaces as a plastic material is beneficial during cauterizing, both to minimize heat transfer to the surgeon's hand and/or the vaginal tissue at unwanted locations, and for easier grasping and handling by the surgeon.

According to the invention, a master handle can be autoclaved and reused almost indefinitely, whereas bags of sterile blades can be easily manufactured, stored, and disposed of after use.

DESCRIPTION OF THE PREFERRED EMBODIMENT

Figure 1:
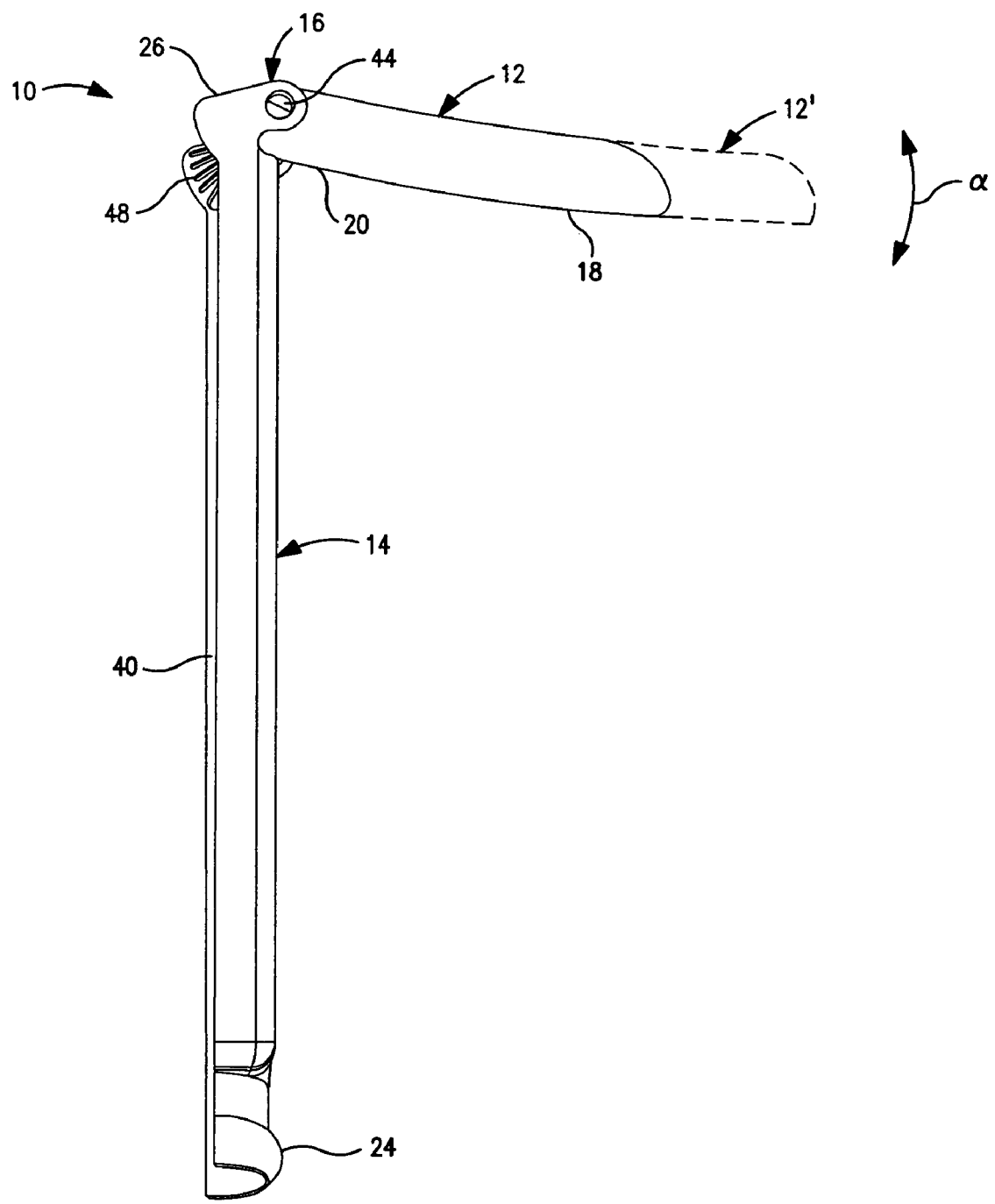
FIG. 1 is an elevational, partly tilted side view of the vaginal speculum according to the preferred embodiment of the invention.

A first embodiment of the invention will be described with reference to the accompanying FIGS. 1-5, with the overall device illustrated in FIGS. 1 and 2. The speculum 10 has a blade 12 attached to a handle 14 with an adjustable connection 16 therebetween. The blade has a distal end 18 and a proximal end 20, and the handle has a weighted distal end 24 and a proximal end 26. The connection 16 is between the proximal end 20 of the blade and the proximal end 26 of the handle.

The blade 12 has a concave curvature in the base 28, and upturned sidewalls 30, 32, thereby providing a channel having an open front. The overall length, width, and contouring are adapted to penetrate and fully enter a vagina, such that the channel provides access for surgical instruments or diagnostic devices, as is well known. The proximal end of the blade 12 has a pair of transversely spaced apart connector tabs 34, the purpose of which will be discussed further below. It should be appreciated that one can readily project a centerline through the channel, thereby defining a blade axis.

Figure 3:
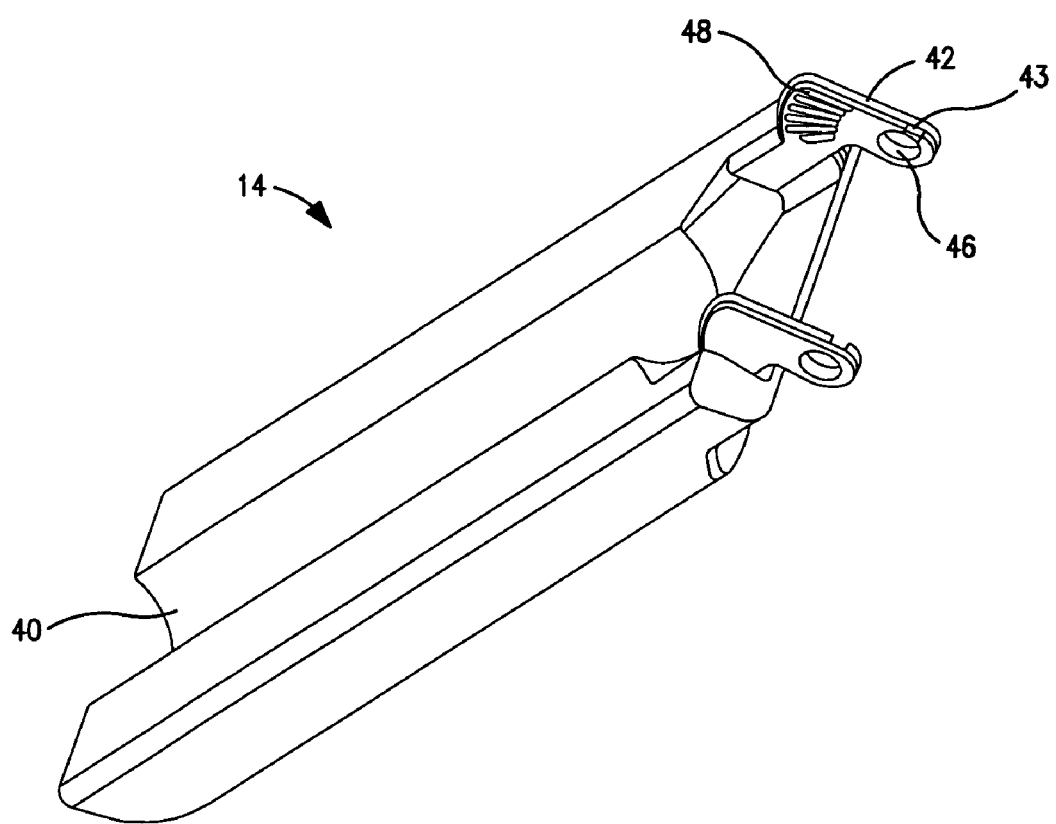
FIG. 3 is a perspective view of the upper portion of the speculum handle, where the connection is made to the blade.

The handle 14 preferably has a flat back 36 and substantially square side walls 38. As shown in FIG. 3, the front of the handle preferably has a semicircular channel or the like 40 through which a centerline can establish a handle axis that intersects the blade axis at a particular included angle and together define a vertical plane of angulation. The proximal end 26 of the handle has a pair of transversely spaced apart connector bosses 42, for connection to the spaced apart tabs 34 on the blade 12.

In use, the surgeon would hold the speculum in one hand, with the front of the handle facing the surgeon and the front of the blade extending away from the surgeon for entry into the vagina. After insertion of the blade 12, the base 28 bears against the lower surface of the vagina, with much of the weight of the handle 14.

The preferred connection is effectuated between a mounting hole 46 on each connector boss 42, and a pivot pin 44 projecting outwardly from each connector tab 34 at the proximal end of the blade 12. This connection is easily made and broken in the surgical field by a surgeon. Preferably, the inside surface of the bosses 42 have channels 43 or the like, to facilitate the sliding of the pivot pins 44 into the holes 46. For example, if the pin 44 has a nominal diameter D, the ends of the pins can be semi-circular with a maximum width transverse to the diameters, of D/2. The channel in the boss can have a width substantially equal to D/2 whereby when the blade 12 is substantially coaxially aligned with the channel, the pin can slide through the channel, into the hole 46. Upon rotating the blade axis away from the handle axis, the pin will rotate within the hole 46 and will be trapped in the hole until the blade is again coaxially aligned with the handle.

Not only is the selected blade easily attachable to the handle, but the surgeon has flexibility to select the ideal angulation between the blade and the handle. The spaced apart bosses 42 have a fan shaped region adjacent the mounting holes 46, on which are formed a plurality of detents or slots 48 as shown in more detail in FIGS. 3 and 4. As shown in FIG. 5, the spaced apart connector tabs 34 also have an enlarged portion adjacent the pivot pins 44 on which is carried a tooth or the like 52. When the connector bosses overlap the connector tabs and the mounting pins 44 are in the mounting holes 46, the tooth 52 is situated in one of the plurality of angulation detents 48. This relationship is analogous to a ratchet, such that the blade can either be attached, or once attached, adjusted, to any one of a plurality of angles between the angle axis and the blade axis.

Figure 4:
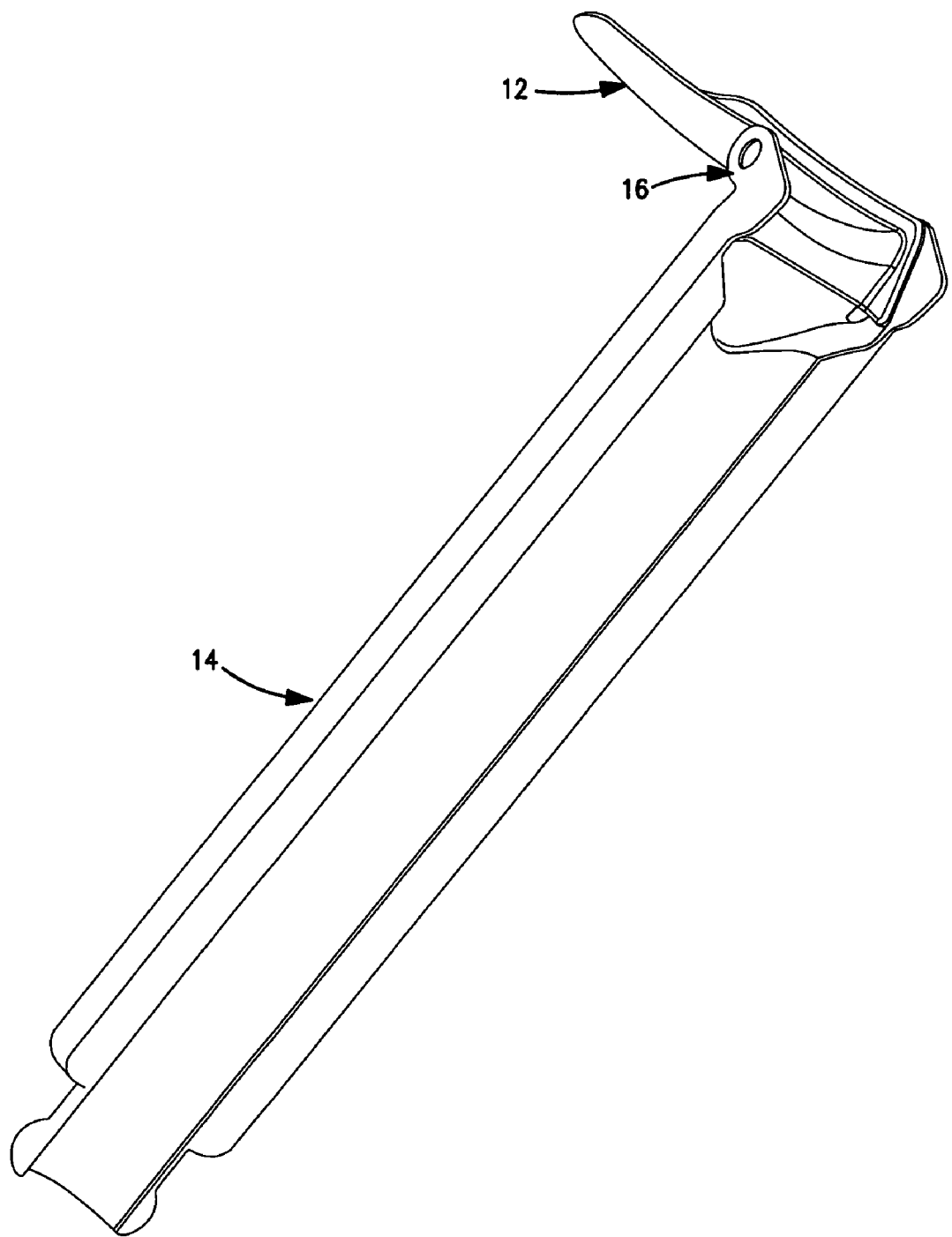
FIG. 4 is a perspective view of the speculum, showing another side and the back.
Figure 5:
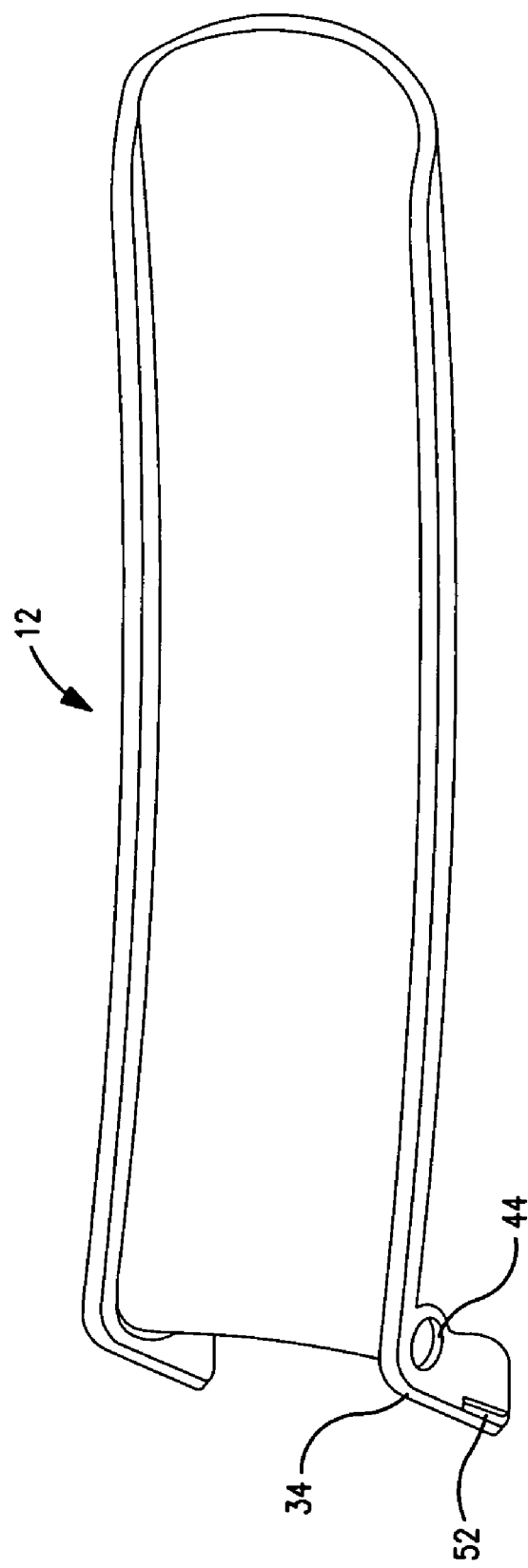
FIG. 5 is an illustrative view of one blade suitable for connection to the handle.
Figure 6:
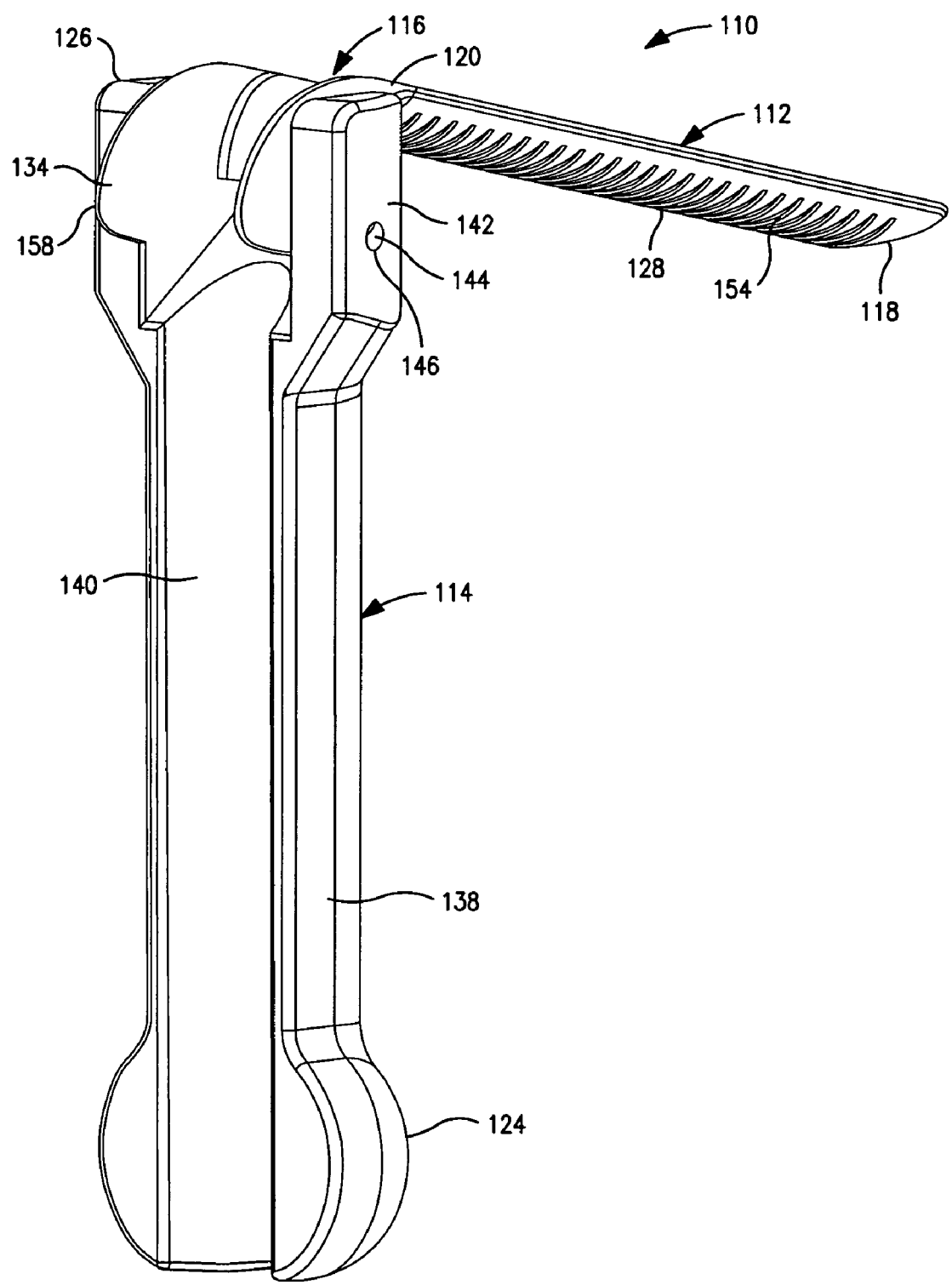
FIGS. 6-9 are show another embodiment with views corresponding to FIGS. 1-3 and 5, respectively.
Figure 7:
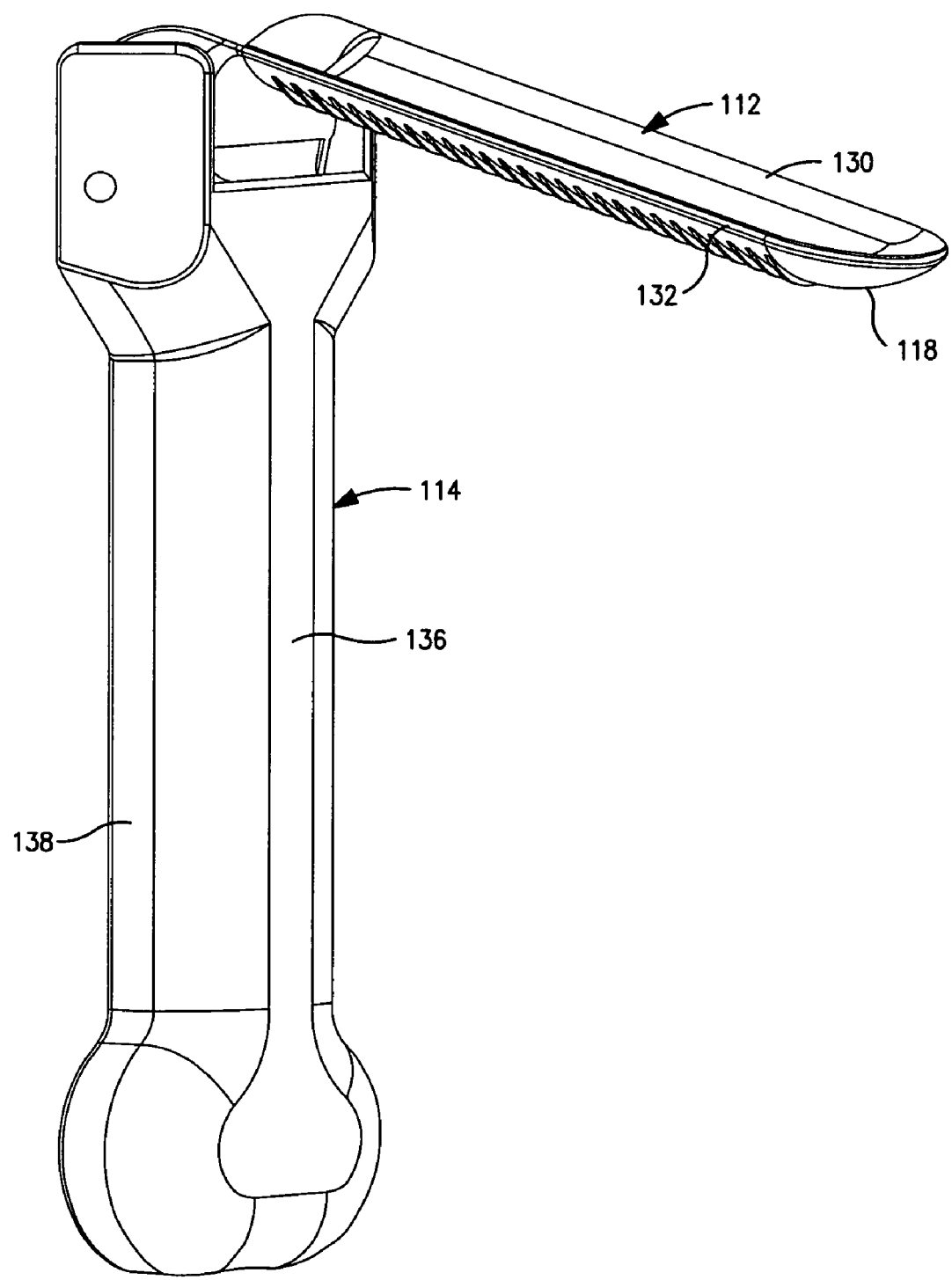

FIG. 4 also shows a continuity of the channel 40, at the adjustable connection 16, so that cables, instruments or the like that are within channel 40 can easily bend around the connection onto the channel of the blade.

Of course, the mounting bores 46 and associated mounting pins 44 could be provided on the other of the bossed or tabs, with equivalent functionality and the tabs could be outside rather than inside the bosses.

Figure 2:
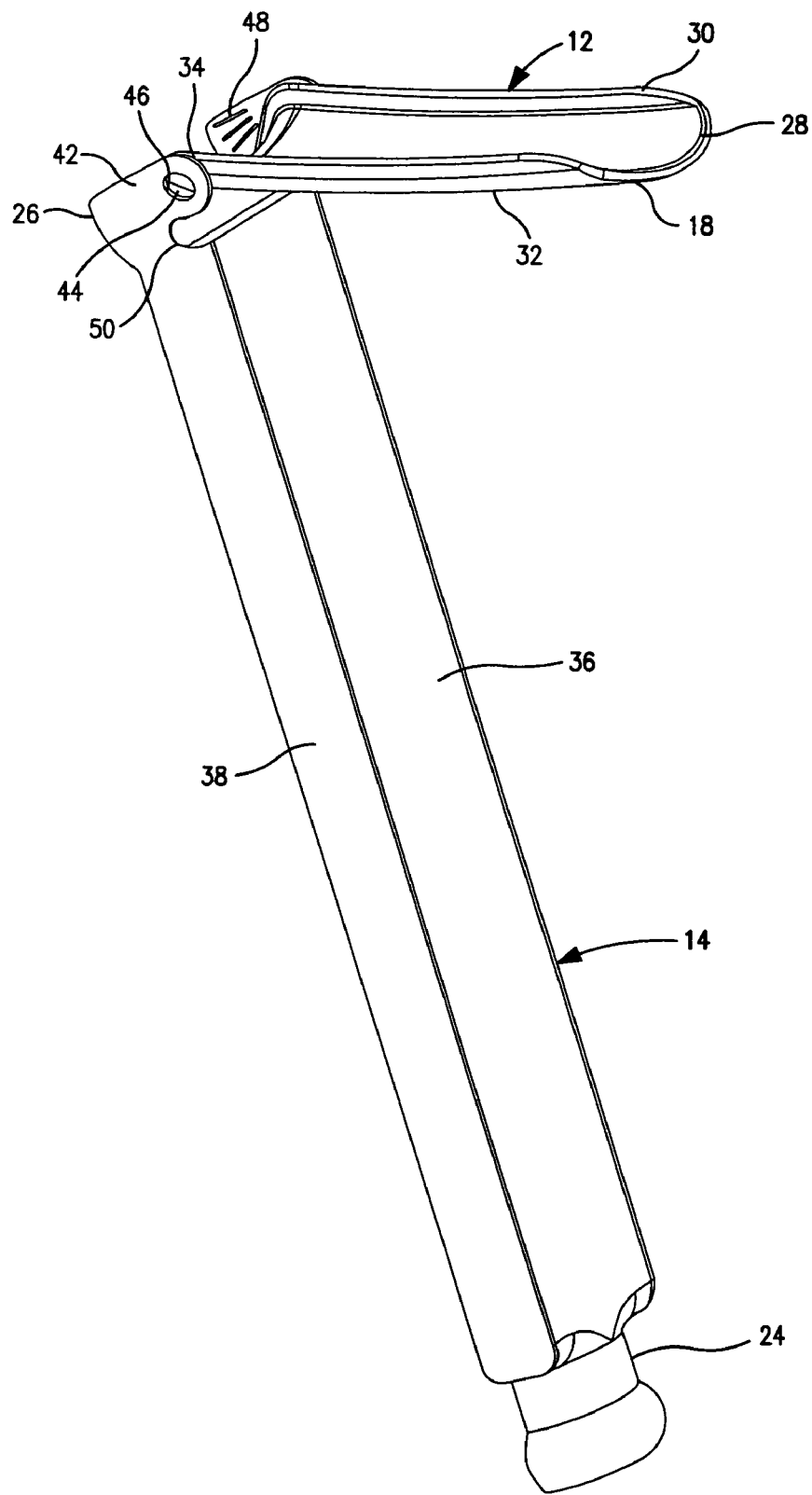
FIG. 2 is an elevational, partly tilted view, showing one side and the front of the speculum.

Not only can a particular blade be secured in any one of the plurality of angular relationship relative to the handle, but as shown in FIG. 1, the surgeon can have a plurality of blades, each having a different length, width, and/or contouring. One such additional blade is shown at 12', having the same width and contour as blade 12, but having a substantially longer length.

The manual adjustablility of the angulation between the blade and the handle is indicated at alpha in FIG. 1. Even if the pivoting connection is permanent, the angulation feature still provides significantly greater flexibility to the surgeon than is available with conventional weighted specula. However, the preferred embodiment includes manual interchangeability and angulation. In this context, "manual" means that no tool, such a wrench, screw driver, hammer, or the like, is needed to make the adjustment.

FIGS. 6-9 illustrate another embodiment of the invention. This embodiment of the weighted speculum 110 also has a blade 112 attached to a handle 114 with an adjustable connection 116 therebetween. The blade has a distal end 118 and a proximal end 120, and the handle likewise has a distal end 124 and a proximal end 126. The connection 116 is between the proximal end 120 of the blade and the proximal end 126 of the handle.

The blade 112 has a concave curvature in the base 128, and upturned sidewalls 130, 132, and an upturned, spoon type, rather than open, front. The proximal end of the blade 112 has a pair of transversely spaced apart connector tabs 134. The tabs in this embodiment are larger and more flexible, enhancing the surgeon's ability to quickly change the angle, or substitute a new blade. The underside of the blade has a multiplicity of spaced apart, transverse projecting ribs 154 that help retain the blade within the vagina during the medical procedure.

Figure 8:
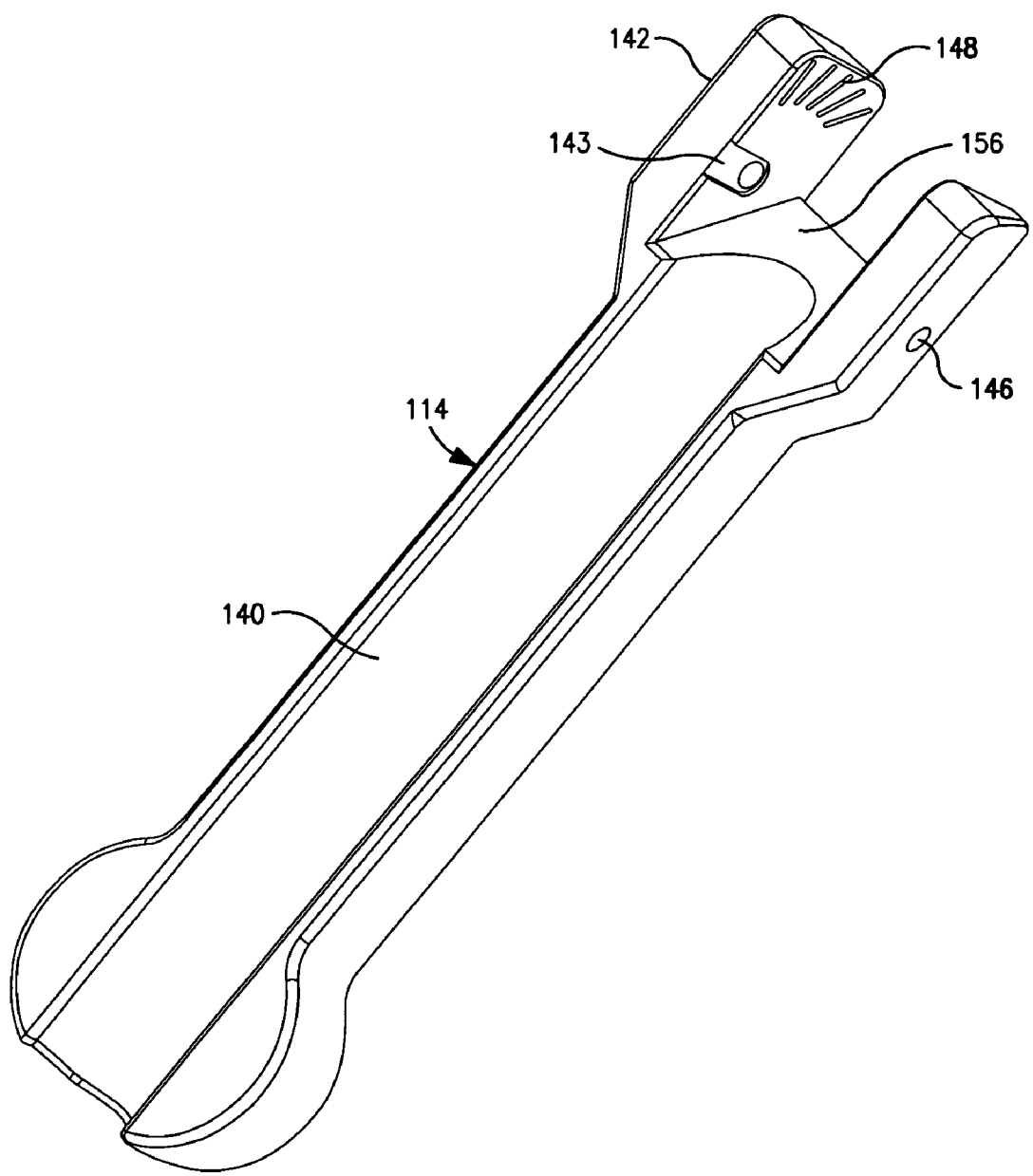

This handle 114 has contoured back and side walls 136, 138. As shown in FIG. 8, the front of the handle preferably has a semicircular channel or the like 140 through which a centerline can establish a handle axis that intersects the blade axis at a particular included angle. The proximal end 126 of the handle has a pair of transversely spaced apart connector bosses 142 that extend in parallel with the handle axis, rather than transversely as in the previously described embodiment, for connection to the spaced apart tabs 134 on the blade 112. A ramp 156 extends obliquely to the axis at the base of the bosses, rising from the front toward the back of the handle.

The connection is effectuated between a mounting hole 146 on each connector boss 142, and a pivot pin 144 projecting outwardly from each connector tab 134 at the proximal end of the blade 112. This connection is easily made and broken in the surgical field by a surgeon. Preferably, the inside surface of the bosses 142 have channels 143 or the like formed transversely to the handle axis, to facilitate the sliding of the pivot pins 144 into the holes 146.

Figure 9:
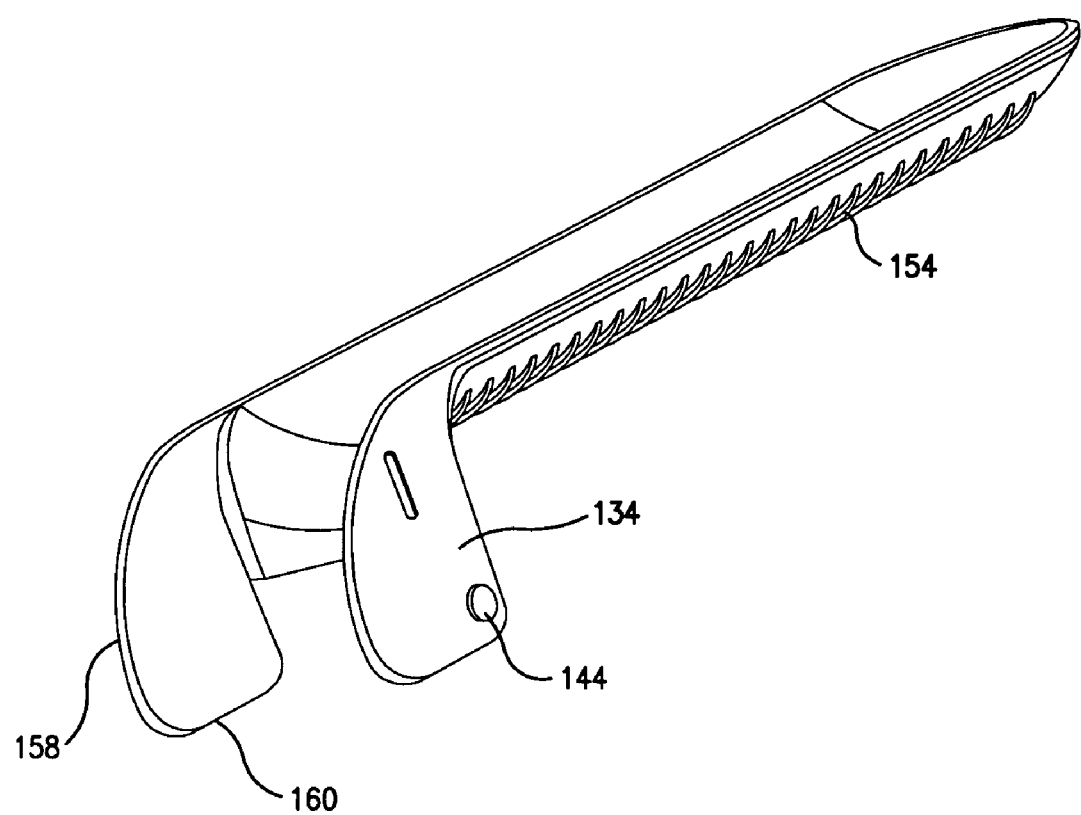

The spaced apart bosses 142 have a region above the mounting holes 146 along the handle axis, on which are formed a plurality of detents or slots 148. As shown in FIG. 9, the spaced apart connector tabs 134 also have an enlarged portion for the pivot pins 144 and a tooth or the like 152 which is spaced generally above the pin, i.e., the spacing direction is transverse to the blade axis. When the connector bosses overlap the connector tabs and the mounting pins 144 are in the mounting holes 146, the tooth 152 is situated in one of the plurality of angulation detents 148. The blade can either be attached, or once attached, adjusted, to any one of a plurality of angles between the handle axis and the blade axis. The contouring of the tabs 134 is convex at the back 158 and substantially flat at the bottom 160, such that shape of the tabs 134 permits the edge of the tab to be placed on the ramp 156 of the handle for easy alignment of the pins 144 with the channels 143 and sliding through until the pins snap into the mounting holes 146. When the blade and handle are connected, the back 158 of the tabs extends beyond the boss (see FIG. 6), whereby the surgeon can squeeze the tabs toward each other to facilitate change of blade or angulation. The edge of the tabs also provides support as the tabs 134 are pivoted to adjust the angulation, facilitating angulation adjustment while the blade is in the vagina.

Those familiar with this field of technology can readily appreciate the significant advantages arising from the use of a universal handle that can be autoclaved and reused, in conjunction with a wide range of blade sizes, contours, and angulation that can be quickly selected and implemented in the surgical field. For example, once the patent is in the proper position for examination or surgery, the surgeon can open a bag of sterilized blades of varying sizes and/or contours, from experience and a modest degree of trial and error, select the blade that is most suitable for the particular procedure to be performed. Upon selection of that blade, the surgeon can then easily attach that particular blade to the handle and at a best-guess angulation. Upon insertion of the blade into the vagina, the angulation can be checked and, if necessary slight adjustments made. With the present invention, such adjustment can, be made while the blade remains in the vagina. Optionally, the blade can be removed to make the adjustment.

In another approach, the surgeon can make an educated selection of a particular blade and angle that should be suitable, and connect such blade to the handle at such angle. The blade can then be inserted in the vagina and the handle positioned in accordance with the contemplated surgical procedure. If the combination of blade length and angulation are not ideal, the surgeon can adjust the angulation either while the blade is in the vagina or after the blade has been removed.

In a relatively simple kit, three blades of different length and proportional contouring would be available to the surgeon. Whether only one, or all three are tried before deciding on the final combination of blade and handle, the cost-effectiveness of quickly achieving an optimum fit while using only one component that requires autoclaving (the handle), and disposing of rather than requiring autoclaving of the blades, should be very attractive.

It should be appreciated that the invention also encompasses embodiments that may not provide all the advantages or achieve all the objectives set forth herein. For example, at a first, basic level, the angular adjustablility of a fixed blade, or the combination of a universal, reusable handle with a uniform, disposable blade, achieves advantages relative to current practice. Moreover, in the next level of innovation, such uniform, disposable blade is adjustable to any one of a range of angles relative to the handle. Yet another aspect of improvement relative to the basic innovation, is in the form of a kit comprising a plurality of blades of different size, angle of projection and/or contouring that are interchangeably connectable to a universal handle. Of course, the most advantageous embodiment of the invention includes interchangeability of blades of different size and/or contour, with each blade also being adjustable as to angulation relative to the handle.

It should also be appreciated that the use of tabs and bosses with pivot pin for making the connection between the blade and the handle as described above, is only one of many techniques for implementing the invention. This particular connection achieves three functions between the tabs and the bosses:

(1) attaches the blade to the handle so that they do not separate, (2) provides a rotational degree of freedom for permitting adjustment of the angulation; and (3) provides fixation of the angle as selected by the surgeon.

In the illustrated embodiments, the interaction of the pivot pins 44, 144 and the mounting holes 46, 146 achieves functions (1) and (2), whereas the detents 48, 148 and associated tooth 52, 152 provide the function (3).

Figure 10A:
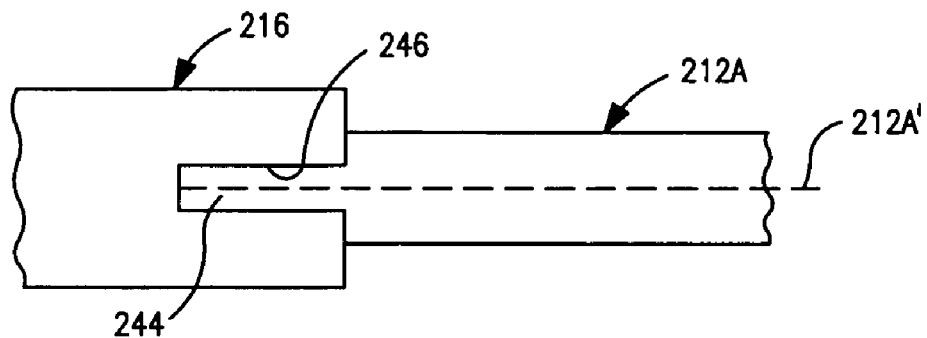
FIGS. 10A and 10B are schematic representations of one possible technique for the universal mounting of interchangeable blades having different angles relative to the handle.
Figure 10B:
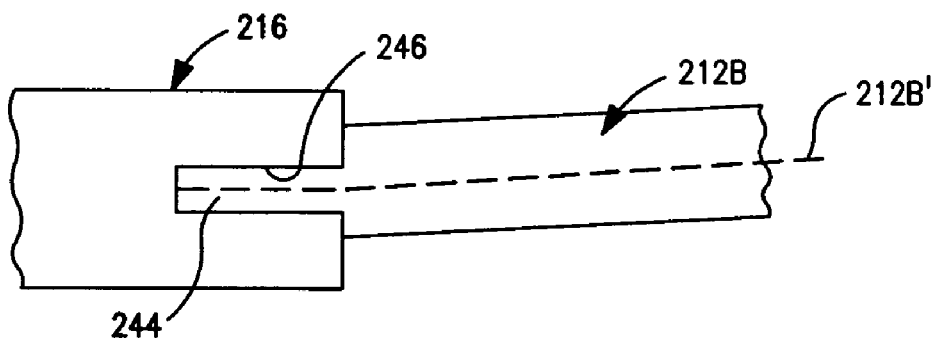

In less comprehensive embodiments, function (2) may not be present at the connection. For example, for any given blade, the attachment to the handle establishes a constant angulation. In one such implementation, a plurality of blades having different lengths would all be securable interchangeably, but at the same angle, relative to the handle. In another variation, the kit contains blades of three different sizes, with each such size having three angle variations that are determined by the size and/or shape of the blade structure that connects to the handle. This attachment concept is illustrated in FIG. 10. FIG. 10A is a schematic representation of a connection 216 on the handle having a slot or other receiving cavity 246 in which a connecting projection 244 associated with blade 212A is securable, thereby establishing a particular orientation of blade axis 212A'. FIG. 10B shows the same connecting structure 216 on the handle and the same projection 244 on the blade 212B, but in this instance the orientation of the blade relative to the projection 244 is along a different axis 212B'. In this manner, several blades having the same length and/or contour are available to provide a different angulation for the speculum, while using the same mounting on the universal handle.

Other ways of achieving the same effect as described with respect to FIGS. 10A and 10B are also possible, such as a variable wedge projection corresponding to projection 244 on the blade with a constant or varying inverse wedge corresponding to 246 on the handle, with associated clamping for securing the blade to the handle, e.g., bayonet or similar mounts.

Furthermore, other functionally equivalent, manually adjustable techniques for making, tightening or loosening the connection for one or both of blade interchangeability or blade angulation, should be considered as falling within the scope of the invention. These can include bolts and associated wing nuts, spring pin detents, or ratchet rollers. These may not facilitate the speed of change afforded by the preferred embodiments, but to the extent these fall within the literal and equivalent scope any claims, they should be deemed within the scope of the invention.

The invention claimed is:

1. A weighted vaginal speculum comprising:
   an elongated handle having distal and proximal ends along a handle axis, said distal end of the handle including a weight, wherein the proximal end of the handle has a pair of connector bosses formed thereon, spaced apart transversely to the handle axis and extending in parallel with the handle axis, and a ramp surface between the bosses;
   an elongated blade having a free distal end and a proximal end connected to the proximal end of the handle, and a blade length between the ends along a blade axis, wherein the proximal end of the blade has a pair of connector tabs formed thereon and spaced apart transversely to the blade axis, each connector boss is connected to and overlaps a connector tab and the blade is contoured along said length to penetrate and fully enter a vagina while providing surgical access;
   first means, for pivotally retaining the blade to the handle, cooperating at a first location between the bosses and tabs, and second means, for setting said selected angle, cooperating at a second location between the bosses and tabs;
   wherein the first means include a pivot pin engaging a mounting hole adjacent the ramp, the second means include a tooth cooperating with detents axially outward on the bosses from the first means, and the tabs include edges that bear on said ramp; and
   wherein the connection between the handle and the blade is manually selectively detachable and reattachable.

2. The vaginal speculum of claim 1, wherein
   said distal end of the handle includes a weight extending along said handle axis
   only said blade is adapted to penetrate, fully enter and be self-retained in a vagina while the handle hangs in free space beneath the vagina, thereby providing surgical access; and
   the underside of the blade has a plurality of ribs for retaining the blade within the vagina while the weighted handle hangs by gravity and thereby pulls the blade downward against the lower surface of the vagina.

3. The vaginal speculum of claim 1, wherein the underside of the blade has projections for retaining the blade within the vagina while the weighted handle hangs by gravity and thereby pulls the blade downward against the lower surface of the vagina.

4. The vaginal speculum of claim 1, wherein the tabs include flange portions projecting from the bosses along the blade axis, for squeezing by the thumb and forefinger to at least partially disengage said second means whereby the angle can be adjusted without disengaging said first means.

5. The vaginal speculum of claim 1, wherein the handle is metal permanently encapsulated in a heat resistant insulating material and the blade is a solid plastic material having projections on its underside for retaining the blade within the vagina.

6. The vaginal speculum of claim 1, as part of a kit including a second elongated blade adapted to penetrate and fully enter a vagina while providing surgical access, having a free distal end and a free proximal end interchangeably connectable to the proximal end of the handle with structure having identical means as said blade at the connection for selectively detaching and reattaching said second blade at any one of a plurality of angles between the handle axis and the blade axis, wherein the second blade differs from said blade by at least one of length along a blade axis, width transverse to the blade axis, or contour along said length.

7. A method of selecting a vaginal speculum kit for use on a patient in the field of surgery during a surgical procedure, comprising:

selecting a sterile universal handle having a handle axis and means for interchangeable mounting of a vaginal speculum blade;

selecting a first blade from a group of sterile blades in the surgical field that each have a blade axis but differ from each other by at least one of length, width, or contour;

attaching the first blade to the handle, thereby establishing an angle between the handle axis and the axis of the first blade;

inserting the first blade in the patient's vagina whereby the handle hangs substantially vertically outside the vagina, and evaluating the quality of the fit of the first blade in the vagina;

depending on the quality of the fit, either (a) (1) removing the first blade from the handle, selecting and attaching a second blade to the handle, inserting the second blade in the patient's vagina, and evaluating the quality of the fit of the second blade; and (2) performing the surgical procedure while the second blade is in the patient's vagina and the handle hangs substantially vertically outside the vagina, or (b) (1) adjusting the angle of the first blade relative to the handle, inserting the adjusted first blade in the patient's vagina, and evaluating the quality of the fit, and (2) performing the surgical procedure while the adjusted first blade is in the patient's vagina and the handle hangs substantially vertically outside the vagina.

8. The method of claim 7, wherein all blades from said group that were handled are disposed of and said handle is sterilized for reuse with another group of speculum blades.

* * * * *